United States Patent [19]

Milkowski et al.

[11] 4,244,869
[45] Jan. 13, 1981

[54] BENZODIAZEPINE DERIVATIVES AND PROCESS OF MAKING THEM

[75] Inventors: Wolfgang Milkowski, Burgdorf; Renke Budden, Peine; Siegfried Funke, Hanover; Rolf Hüschens, Hanover; Hans-Günther Liepmann, Hanover; Werner Stühmer, Eldagsen; Horst Zeugner, Hanover, all of Fed. Rep. of Germany

[73] Assignee: Kali-Chemie A.G., Hannover, Fed. Rep. of Germany

[21] Appl. No.: 888,151

[22] Filed: Mar. 16, 1978

Related U.S. Application Data

[62] Division of Ser. No. 725,989, Sep. 23, 1976, Pat. No. 4,098,786.

[30] Foreign Application Priority Data

May 3, 1972 [DE] Fed. Rep. of Germany ....... 2221558
May 10, 1975 [DE] Fed. Rep. of Germany ....... 2520937

[51] Int. Cl.³ .................. C07D 243/16; C07D 245/06; C07D 243/24
[52] U.S. Cl. ............................................. 260/239 BD
[58] Field of Search ................................. 260/239 BD

[56] References Cited

U.S. PATENT DOCUMENTS 4,096,141   6/1978   Milkonski et al. ............ 260/239 BD

FOREIGN PATENT DOCUMENTS 2353160  11/1974  Fed. Rep. of Germany ... 260/239 BD
2353165  11/1974  Fed. Rep. of Germany ... 260/239 BD
2353187  11/1974  Fed. Rep. of Germany ... 260/239 BD Primary Examiner—Alton D. Rollins
Attorney, Agent, or Firm—Michael J. Striker

[57] ABSTRACT

1,4-Benzodiazepin of the formula

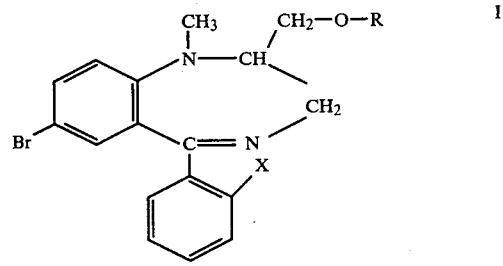

wherein R is a low molecular straight or branched alkyl and X is halogen or trifluoromethyl, and pharmaceutically acceptable acid addition salts of these benzodiazepins. The benzodiazepins are made by heating an acyldiamine in the presence of phosphorus oxychloride at the latter's boiling point followed by reacting the resulting mixture of 7-member and 8-member compounds with an alkali metal alkoxide.

7 Claims, No Drawings

BENZODIAZEPINE DERIVATIVES AND PROCESS OF MAKING THEM

CROSS-REFERENCE TO RELATED APPLICATIONS

This is a division of application Ser. No. 725,989, filed Sept. 23, 1976, now U.S. Pat. No. 4,098,786 granted July 4, 1978 which in turn was a continuation-in-part of application Ser. No. 355,986 filed May 1, 1973 by the same inventors and with the same title as the present application (now U.S. Pat. No. 3,998,809).

BACKGROUND OF THE INVENTION

In the above-noted parent application benzodiazepin compounds have been disclosed which were substituted in the 2-position by various groups including alkoxy methyl groups. Some of these compounds also included methoxy methyl and ethoxy methyl groups in the 2-position. Some of these compounds further were substituted in the 5-position by a 2-chlorophenyl group.

The compounds of the parent application also included 7-bromo compounds which, however, were not substituted in the 2-position by alkoxy methyl.

The compounds of the parent case were shown by animal tests to have anticonvulsive, sedative, muscle relaxant and ataractic activity.

It has now been found that the combination of a 2-alkoxymethyl group with a 7-bromo substitution results in a superior profile of properties. This applies in particular when the 2-alkoxymethyl-7-bromo substituted diazepins are compared with similar 7-chloro substituted compounds.

SUMMARY OF THE INVENTION

The invention accordingly resides in 1,4-benzodiazepin derivatives of the formula

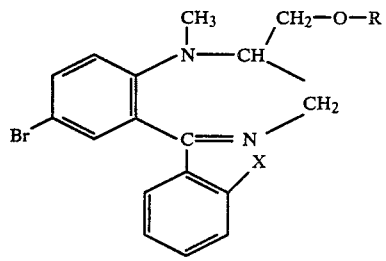

wherein
R is straight or branched alkyl of 1 to 6 carbon atoms, and
X is halogen or trifluoromethyl.

The invention also embraces acid addition salts of these compounds. Particularly preferred are compounds which are substituted in the 2-position by methoxymethyl or ethoxymethyl and in the 5-position by 2'-halogenophenyl, particularly 2'-chlorophenyl. They have a low toxicity and excellent anxiety relieving and sedative activities. This recommends the new compounds particularly for treatment of anxiety, tension, stress, neurotic and unnatural aggressive conditions. The valuable therapeutic properties can be taken advantage of without the disadvantage of a strong sedative action which frequently results in impairment of the perception and awareness as present in fully awake condition. This is important for use as daytime tranquilizers.

The new compounds in addition have a distinctly improved anticonvulsive effect. They furthermore show a distinctly better dosage interval between the anxiety and tension releasing as well as anti-aggressive components and the component which affects the muscle tone. This again is important for the ambulatory treatment of mental patients.

The invention also embraces a method of producing a 2-substituted 1,4-benzodiazepin of the formula

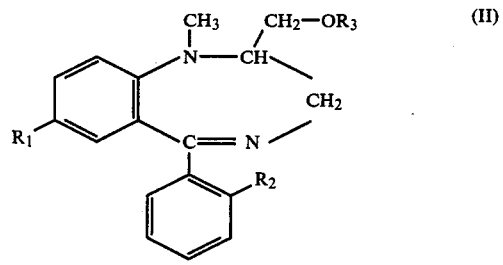

and acid addition compounds thereof, in which
R₁ is hydrogen or halogen,
R₂ is hydrogen, halogen or trifluoromethyl and
R₃ is hydrogen or alkyl of 1 to 6 carbon atoms, the said method comprising
(1) reacting an acyldiamine of the general formula

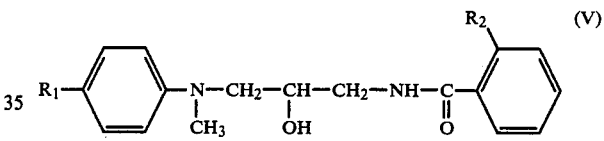

in which R₁ and R₂ have the meaning as above, with an excess of phosphorus oxychloride which is calculated to maintain the temperature throughout the reaction at the boiling point of the phosphorus oxychloride,
(2) separating the mixture of isomeric compounds thus obtained of the formulae

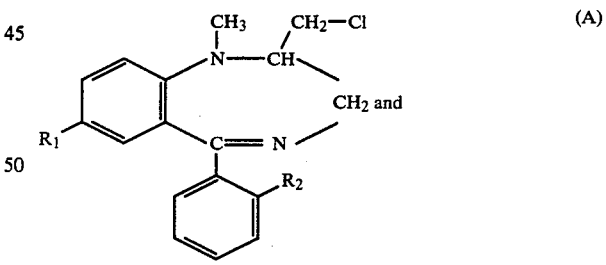

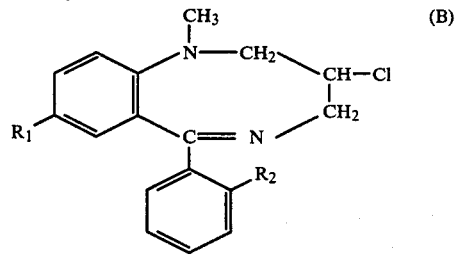

in which R₁ and R₂ have the meaning as above, and
(a) reacting it in a solvent at elevated temperature with an alkali metal alkoxido to form a compound of the general formula II in which R₃ is an alkyl group or (b) reacting the said mixture in a solvent at elevated temperature with an alkali metal hydroxide or an alkali metal carbonate or first reacting it with an alkali metal acetate and then with a dilute alkali metal hydroxide solution so as to form a compound of general formula II in which $R_3$ is hydrogen.

DESCRIPTION OF THE INVENTION AND SPECIAL EMBODIMENTS

The pharmacological properties of the compounds of the invention are shown in the following tests involving animal experiments. For comparison there are used (1) 7-chloro-1-methyl-2-methoxymethyl-5-(2'-chlorophenyl)-1H-2,3-dihydro-1,4-benzodiazepin in the form of its hydrochloride, one of the compounds disclosed in the parent application and (2) diazepam, a common drug in this area of medical practice.

The pharmacological test methods employed are the following:

(1) Acute toxicity

The acute seven-day toxicity is determined by a single application per os and intraperitoneally to white fasting NMRI mice. The computation of the $LD_{50}$ values was effected via EDV by a probit analysis (Cavalli-Sforza, publisher Gustav Fischer, 1964, Grundbegriffe der Biometrie).

(2) Anti-convulsive properties (a) Pentetrazol induced convulsions

The compounds were tested after per oral administration to groups of six mice each. Sixty minutes after application of the test compounds pentetrazol was injected subcutaneously at a dosage of 100 mg/kg. The appearance of clonic and tonic convulsions was checked through a total observation time of 45 minutes. The protective effects of the compounds against convulsions were determined in control tests with comparison compounds. The effective dose $ED_{50}$ was computed from the probit logarithmic dosage curves (modified according to J. E. Blum et al. Arzneimittel-Forsch. 23, 377 [1973]).

(b) Maximum electroshock

The test substances were applied orally to the animals. Sixty minutes after application electrodes were fastened to the ears of the mice and an electric shock was effected. The dose was then determined at which in half of the animals tonic contractions in the rear extremities were prevented. The computation of the $ED_{50}$ was again effected by means of the above-noted probit analysis (modified according to J. Swinyard, J. Pharmacol. exptl. Therap.-106, 93 [1952]).

The results obtained by these tests show the anticonvulsive activity of the test substances. According to the medical literature this is an important criteria for the appraising of the clinical effectiveness of tranquilizers.

(3) Anxiety relieving and anti-aggressive activity. Inhibition of the aggressiveness of a mouse caused by isolation.

Before the test the mice were kept for four weeks in strict isolation in single cages. After that time the mice which had been kept in isolation spontaneously attacked other mice which were introduced then and which had not been isolated. The test substances were administered to the isolated mice orally. After 30 minutes the dose was determined which in 50% of the animals resulted in a reduction of the aggressive behaviour (modified according to Weischer and Opitz, Arch. int. Pharmacodyn. 195, 252 [1972]).

The results shown in these tests permit useful conclusions regarding the anxiety, stress and tension-relieving properties of the compound.

(4) Musculotropic properties

This test is called the "test de la traction". In this test the compounds were administered to the mice per os. After 120 minutes the mice were suspended with their front paws from a thin horizontally extending wire. As $ED_{50}$ that dose was determined at which half of the animals did not touch the wire also with their hind paws within a period of 5 seconds (W. Theobald et al. Arzneim. Forsch. 17, 561 [1967]). These tests have the purpose to check the effects on the muscle tone by the compounds.

The $ED_{50}$ values was effected via EDV by a probit analysis.

(5) C.N.S. quieting properties (Prolongation of hexobarbital induced sleep)

The test substance was applied to the mice per os. The animals after 30 minutes received additionally an intravenous injection of 64 mg/kg of hexobarbital. The time was noted at which the animals adopted first the lateral position. The duration of this lateral position was then compared with the control group which had been treated only with hexobarbital.

As $ED_{50}$ that dose was defined at which with one-half of the animals a prolongation of the lateral position occurred by a factor of 4 as against the control group (G. M. Everett, Nature 177, 1238 [1956]).

The compounds tested were the following:

Compound 1: 7-bromo-1-methyl-2-methoxymethyl-5-(2'-chlorophenyl)-1H-2,3-dihydro-1,4-benzodiazepin (as hydrochloride)

Compound 2: 7-bromo-1-methyl-2-ethoxymethyl-5-(2'-chlorophenyl)-1H-2,3-dihydro-1,4-benzodiazepin (as hydrochloride)

Compound 3: 7-bromo-1-methyl-2-methoxymethyl-5-(2'-fluorophenyl)-1H-2,3-dihydro-1,4-benzodiazepin (as hydrochloride)

Standard 1: 7-chloro-1-methyl-2-methoxymethyl-5-(2'-chlorophenyl)-1H-2,3-dihydro-1,4-benzodiazepin (as hydrochloride)

Standard II: 7-chloro-1-methyl-5-phenyl-1,3-dihydro-2H-1,4-benzodiazepin-2-one (diazepam)

The results of these tests are noted in the following Tables 1 to 5.

Table 1 shows the toxicity values and the values for anticonvulsive activity when comparing Compounds 1, 2 and 3 with the two comparison compounds.

TABLE 1

| Compound | $LD_{50}$ p.o. (mg/kg) | Pentetrazol spasm $ED_{50}$ (mg/kg) | Electroshock $ED_{50}$ (mg/kg) |
| --- | --- | --- | --- |
| 1 | 1578 | 0.9 | 3.0 |
| 2 | >1470 | 2.2 | 24.5 |
| 3 | 1580 | 0.5 | 5.0 |
| Standard I | 1779 | 2.0 | 26 |
| Standard II | 887 | 0.5 | 9.0 |

Table 2 shows the results obtained for the anxiety relieving (anxiolytic) and anti-aggressive activity:

TABLE 2

| Compound | Isolation aggressiveness $ED_{50}$ (mg/kg) |
| --- | --- |
| 1 | 3.1 |
| 2 | 4.1 |
| 3 | 10.7 |
| Standard I | 68 |

TABLE 2-continued

| Compound | Isolation aggressiveness ED$_{50}$ (mg/kg) |
|---|---|
| Standard II | 3.6 |

Table 3 shows the results of the muscle coordination test (test de la traction) and for the sedation activity (prolongation of hexobarbital induced sleep).

TABLE 3

| Compound | Test de la traction | Prolongation of hexobarbital induced sleep ED$_{50}$ (mg/kg) |
|---|---|---|
| 1 | 87 | 15.2 |
| 2 | 34.9 | 41.9 |
| 3 | 58.3 | 10.6 |
| Standard I | 163 | 11.7 |
| Standard II | 4.2 | 1.5 |

In Table 4 Quotient 1 is formed by figuring ED$_{50}$ elongation of hexobarbital induced sleep/ED$_{50}$ isolation aggressiveness.

Quotient 2 is formed by ED$_{50}$ test de la traction/ED$_{50}$ isolation aggressiveness.

These two quotients show clearly the superiority of the compounds of the present application exhibited by the distinct spacing between sedative and anxiety-relieving components and show also the desirable relation between muscle relaxation and anxiety-relieving activity.

TABLE 4

| Compound | Quotient 1 | Quotient 2 |
|---|---|---|
| 1 | 4.9 | 28.1 |
| 2 | 10.2 | 8.5 |
| 3 | 0.9 | 5.4 |
| Standard I | 0.17 | 2.4 |
| Standard II | 0.42 | 1.2 |

This superiority is additionally demonstrated by Table 5 which was obtained from Table 4 by taking Standard I=1.

TABLE 5

| Compound | Quotient 1 Standard I = 1 | Quotient 2 Standard I = 1 |
|---|---|---|
| 1 | 28.8 | 11.7 |
| 2 | 60 | 3.5 |
| 3 | 5.3 | 2.3 |
| Standard I | 1 | 1 |
| Standard II | 2.4 | 0.5 |

In summary the pharmacological results appearing from Tables 1 to 5 clearly show the superiority of the compounds of the invention as against the standard compounds. The compounds of the invention in particular have superior anti-convulsive properties and have a distinct reduction of the sedative and muscle relaxing components in favor of the anxiety-relieving and anti-aggressive properties. The compounds of the invention thus have a novel profile of activities and thus constitute anxiolytica (anxiety-relieving compounds) which are definitely superior to the prior art compounds.

PHARMACEUTICAL COMPOSITIONS

The compounds of the formula I and their pharmaceutically acceptable acid addition compounds can be used for pharmaceutical purposes for instance in the form of compositions in which the compounds of formula I are employed with a carrier material which is suited for enteral or parenteral administration and may be inorganic or organic and should be inert. Such materials for instance are water, gelatine, lactose, starch, magnesium stearate, talcum, vegetable oils, gums, polyalkyleneglycols, petrolatum ("Vaseline"), etc.

The pharmaceutical compositions can be used in solid form (for instance as tablets, lozenges, suppositories, capsules) or in liquid form (for instance as solutions, suspensions or emulsions. They may be sterilized and they may include additives such as preservatives, stabilizers, cross-linking or emulsifying agents, salts for modifying the osmotic pressure or buffer compounds. They may also include additional therapeutically active materials.

METHOD OF MAKING

The compounds of the invention can be made by the following method which is suited also for a broader range of products where in formula I above R and X may also be hydrogen and the bromine atom may be replaced by hydrogen or halogen other than bromine.

Accordingly, by this method there may be produced 2-substituted 1,4-benzodiazepins of the general formula

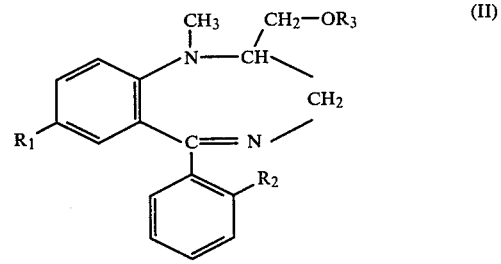

and the acid addition salts thereof, wherein R$_1$ is a hydrogen or halogen atom, R$_2$ is a hydrogen or a halogen atom or the trifluoro-methyl group and R$_3$ is a hydrogen atom or an alkyl group containing 1 to 6 carbon atoms.

Preferred halogen atoms for R$_1$ are chlorine, bromine, and iodine, and for R$_2$ chlorine, fluorine, bromine and iodine, while preferred alkyl groups for R$_3$ are, methyl, ethyl, propyl, isopropyl, butyl or sec. butyl, though amyl or hexyl are also suitable. Some of these compounds are the 7-bromo-2-alkoxymethyl-1,4-benzodiazepins discussed before.

Methods of producing these compounds have been described in above application Ser. No. 355,986, application Ser. No. 685,537 filed May 12, 1976, now U.S. Pat. No. 4,096,141, which is a division of the latter application, and application Ser. No. 355,989 filed May 1, 1973, now abandoned, which discloses an alternative process for making the same compounds (refiled on July 24, 1975 as continuation-in-part of Ser. No. 598,880).

The principal method disclosed in Ser. No. 355,986 comprises reacting, for instance, a 1,4-benzodiazepin of the general formula

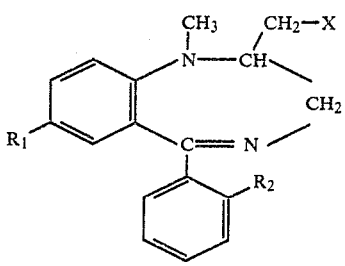

wherein R₁ and R₂ have the same meaning as in formula II and X is a reactive group, preferably a chlorine atom, with an alkali metal hydroxide or alkali metal carbonate in a solvent at elevated temperature to form the 2-hydroxymethyl compounds or with alkali metal alkoxides in the corresponding alcohols to form the 2-alkoxymethyl compounds.

In an alternative method disclosed in above Ser. No. 588,969, now abandoned a 1,5-benzodiazocin of the general formula

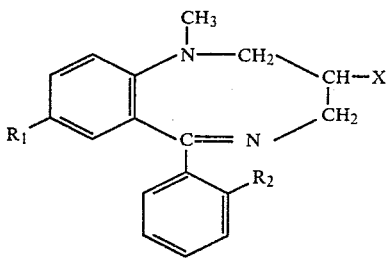

wherein R₁ and R₂ have again the meaning as in formula II and X is a reactive group, preferably a chlorine atom, is produced which can be reacted with an alkali metal hydroxide or alkali metal alkoxide to form the corresponding compound of formula II.

The starting materials for producing compounds of the general formulae III and IV are acyldiamines of the general formula

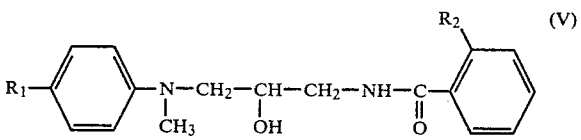

wherein R₁ and R₂ have the above specified meanings. At specific carefully maintained reaction temperatures and, if necessary, in the presence of solvents, these acyldiamines are converted to either benzodiazepins (formula III) or benzodiazocins (IV), the nature of the substituents R₁ and R₂ having a marked effect on the required reaction conditions.

However, the conduct of these reactions calls for a very precise and troublesome method of control. Thus, in order to obtain compounds of the general formula III by the aforesaid method, the acyldiamines are preferably reacted with phosphorus oxychloride. By a suitable choice of the quantitative proportions of the reactants, it is possible to provide the best reaction temperature in the reaction mixture for the formation of the 1,4-benzodiazepins. In particular, compounds of the general formula II in which R₂ is a hydrogen atom, can thus be produced in good yield, preferably at a temperature of from 115° to 125° C. One drawback of this method is that the necessary reaction times are rather long. In the case of some of the substituted acyldiamines the reaction conditions may give rise to an increased formation or resinified secondary products and the difficulty of then further processing the reaction mixture may render the entire procedure uneconomical.

Although it is possible to employ temperatures of around 100° C. in the production of compounds of the general formula IV, which are 1,5-benzodiazocins, satisfactory yields require the use of solvents, such as nitrobenzene, as well as relatively long reaction times. Moreover, the use of nitrobenzene, which is toxic, creates processing difficulties, particularly when working on an industrial scale. In order to suppress the formation of secondary products it has also been proposed to convert the hydroxyl group in the acyldiamine of general formula V to an acyloxy group. However, the temperature needed for reacting such a compound and the likewise relatively long reaction times again tend to produce diminishing yield.

In order to overcome these difficulties and to improve the yield of the acyldiamines it has already been proposed in published German application DT-OS2448259, to react the acyldiamine in several stages by first reacting the acyldiamine for instance with phosphorus pentachloride in dichloroethane to form the corresponding imidoyl halide and then to cyclize this with aluminum chloride in nitrobenzene. It has been ascertained that, in many instances, the cyclization of the imidoyl halide will proceed under milder reaction conditions. In particular, when R₂ is a fluorine atom, better yields result from this procedure than when using the first method. However, it is still a nuisance that the process has to be performed in stages as the use of different solvents and reagents is time-consuming and labor-intensive.

It has now been found that when starting with an acyldiamine of the general formula V, the 2-substituted 1,4-benzodiazepins of the general formula II can be obtained without the need for a complicated reaction procedure, without control for the isolation of the intermediate compounds of above formulae A or B in pure form and without the necessity for conversion of the 2-halomethyl-1,4-benzodiazepins or 3-halo-1,5-benzodiazocines that are thus obtained into the desired compounds.

It has in particular been discovered, surprisingly, that if the acyldiamine of formula V is reacted with phosphorus oxychloride, complete cyclization takes place within a short time, usually in a few hours, and a mixture of compounds of the formulae A and B is obtained, provided an excess quantity of phosphorus oxychloride in the reaction mixture is so chosen that during the reaction the boiling temperature of the phosphorus oxychloride is reached and maintained.

It has also been discovered that the isomer mixture can be directly converted to the required compounds of the general formula II without prior separation into its individual components.

Accordingly, the present invention provides a method of producing a 2-substituted 1,4-benzodiazepin of the general formula

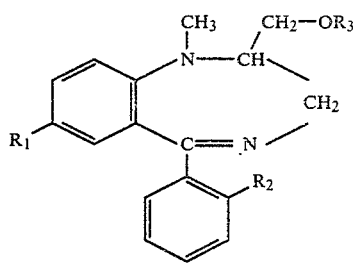

(II)

and acid addition compounds thereof in which, $R_1$, $R_2$ and $R_3$ have the meaning as above wherein an acyldiamine of the general formula V

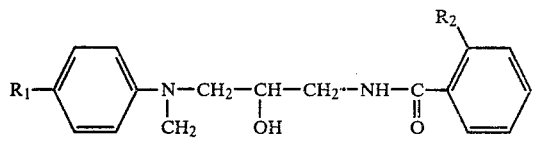

in which $R_1$ and $R_2$ have the above specified meanings, is reacted with an excess of phosphorus oxychloride which is so calculated that throughout the reaction the temperature will be at the boiling point of the phosphorus oxychloride. Thereupon the resulting mixture of isomeric compounds of the general formulae A and B

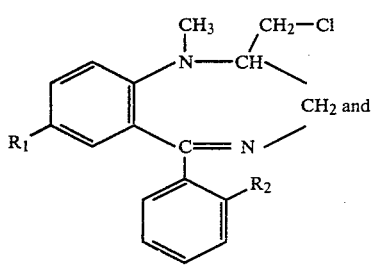

(A)

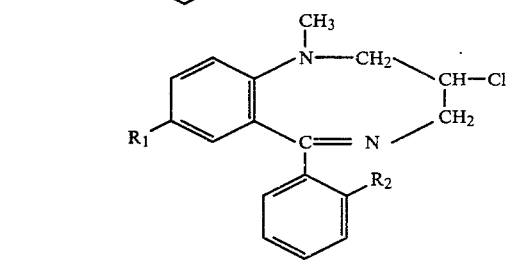

(B)

in which $R_1$ and $R_2$ have the above specified meanings, is separated from the inorganic constituents, and the mixture is then reacted (a) in a solvent at elevated temperature, preferably within a temperature range of 50° to 150° C. with an alkali metal alkoxide to form a compound of the general formula II in which $R_3$ is an alkyl group or (b) is reacted in a solvent at elevated temperature with an alkali metal hydroxide or alkli metal carbonate or is first reacted with an alkali metal acetate and then with a dilute alkali metal hydroxide solution to form a compound of general formula II in which $R_3$ is a hydrogen atom. We prefer temperatures between about 50° to 150° C.

The quantity of phosphorus oxychloride necessary for adjusting the temperature in the reaction mixture to its boiling point can be readily determined, as will be understood from the Examples described hereinafter.

The conversion of the isomer mixture to the corresponding 2-hydroxymethyl- or 2-alkoxy-methyl-1,4-benzodiazepin of the general formula II proceeds, possibly after preliminary crude purification, under reaction conditions, which have already been described for the production of these compounds, by reacting the mixture of compounds of formulae III and IV with the corresponding nucleophilic reactants, namely alkali metal alkoxides, alkali metal carbonates, alkali metal hydroxides or alkali metal acetates, the sodium or potassium compounds being usually preferred. Solvents which are suitable when alkali metal alkoxides are used, are the corresponding alcohols. However, the reaction can also be performed in other suitable solvents containing no protons, such as dimethyl sulphoxide, dimethyl formamide and hexamethyl phosphoric acid triamide.

If alkali metal hydroxides or alkali metal carbonates are used to prepare the corresponding 2-hydroxymethyl derivatives, such reagents are generally used in the form of aqueous solutions, if necessary, together with a water-miscible solvent such as dioxane or tetrahydrofuran. If, however, an alkali metal acetate is used to form the hydroxymethyl derivative, the mixture of isomers is usefully first treated with such an acetate in the presence of a solvent such as dimethylformamide and then with a dilute solution of an alkali metal hydroxide, usefully in the presence of methanol. If desired, these conversion reactions may be carried out in two-phase systems. Suitable reaction temperatures are the relevant reflux temperatures, preferably within a temperature range of 50° to 150° C.

The starting materials may be the acyldiamines of general formula V in which the rings may already contain the substituents desired in the final product. Alternatively the substituent $R_1$, provided it is chlorine, bromine or iodine, may be introduced subsequently, i.e. after the cyclization reaction or after the production of a 2-substituted 1,4-benzodiazepin of the general formula II in which $R_1$ is a hydrogen atom, by reaction with a suitable halogenating agent, N-bromo- and N-chlorosuccinimide being particularly suitable halogenating agents for bromine and chlorine and iodine monochloride being a particularly suitable halogenating agent for the introduction of iodine.

The present method has the advantage over previously proposed methods that the production of the 2-substituted 1,4-benzodiazepins involves less work, i.e. that it does not involve complicated reaction control and purification procedures, and that reaction times are shorter. Moreover, the yields are generally higher than in the previously proposed methods. The present method is particularly suitable for the production of those compounds in which $R_2$ is a halogen atom or a trifluoromethyl group. This could not have been foreseen, especially not in the light of the fact that cyclization to form compounds of both formula A and formula B requires long reaction times and that only unsatisfactory yields of a number of $R_2$-substituted compounds of general formula II can be obtained. The good yields achieved and the available range in the production of the desired compounds are also astonishing because it is the usual observation in preparative chemistry that considerable losses in yield are unavoidable because of uncontrolled and complex side reactions when mixtures or only partially purified raw materials are used.

By means of the reactions as described it is possible to obtain the compounds of formula II as a free base either directly from the reaction mixture or in conventional form from the acid addition product, preferably the hydrochloride. This is done by hydrolysis upon use of a base such as sodium hydroxide, sodium carbonate or an ammonia solution. Starting from the free base it is also possible to make the desired acid addition product according to conventional processes.

If the compounds are intended for use as intermediates in making other compounds or in connection with nonpharmaceutical use the toxicity or lack of toxicity of the salts is without consequence. However, if the compounds are used for pharmaceutical purposes they are preferably used as nontoxic acid addition compounds. However, it is intended to embrace in the scope of this invention both toxic and nontoxic salts.

Acids which can be used for making the preferred nontoxic acid addition compounds are those which form salts with the free base, and wherein the anions of the salts in therapeutic doses are innocuous for human beings so that the useful physiological properties of the bases are not vitiated by side effects of the acidic components. In order to obtain the salts the bases are reacted with the necessary amount of organic or inorganic acid in a water miscible solvent such as ethanol or isopropanol. The salts are then recovered by concentration and cooling. The base can also be reacted with an excess of water in a solvent which is not water miscible such as diethylether or diisopropylether. In this case the salt immediately precipitates.

Examples of organic acid addition salts are for instance those formed with maleic, fumaric, benzoic, ascorbic, succinic, methane sulfonic, acetic, propionic, tartaric, citric, lactic, malic, cyclohexanesulfamic, p-aminobenzoic, toluenesulfonic, glutamic or stearic acid. Inorganic salts can for instance be formed with hydrochloric, hydrobromic, sulfuric, sulfaminic, phosphoric or nitric acid.

The use of the nontoxic salts of the compounds of Formula II in pharmaceutical compositions has the advantage over the use of the base that the salts normally are water soluble.

EXAMPLES

The following examples will illustrate the invention without limiting its scope. They involve processes which result in the desired compounds without laborious purification and time-consuming isolation of intermediate products.

EXAMPLE 1

70 g of $N_1$-phenyl-$N_1$-methyl-$N_2$-(2'-chlorobenzoyl)-2-hydroxy-1,3-diaminopropane are refluxed in 350 ml phosphorus oxychloride for $2\frac{1}{2}$ hours. The excess phosphorus oxychloride is then distilled off in a vacuum. The residue is taken up in 500 ml chloroform and is thoroughly stirred successively with 200 g ice, 200 ml water and 200 ml concentrated sodium hydroxide. The organic phase is thereafter separated, washed neutral with water, dried on sodium sulfate and concentrated by evaporation. The residue is stirred for 3 hours with 250 ml ether, reacted with 100 g of γ-alumina and filtered. After distilling off the ether there remain 50 g of a crude product that consists of a mixture of 1-methyl-2-chloromethyl-5-(2'-chlorophenyl)-2,3-dihydro-1H-1,4-benzodiazepin and 1-methyl-3-chloro-6-(2'-chlorophenyl)-1,2,3,4-tetrahydro-1,5-benzodiazocin.

This crude product is then taken up in 750 ml methanol in which 4 g of sodium have been dissolved and is heated for 5 hours upon reflux. At the end of this time the solvent is distilled off, the residue is dissolved in 250 ml toluene and washed neutral with water. The organic phase is thoroughly stirred with 200 g $Al_2O_3$ of the activity range II–III, basic (Merck Standard) and is then filtered. The solvent is distilled off. The residue (43 g) which consists of 1-methyl-2-methoxymethyl-5-(2'-chlorophenyl)-2,3-dihydro-1H-1,4-benzodiazepin is dissolved in 800 ml methylene chloride and heated with 24.5 g of N-bromosuccinimide for 24 hours upon reflux. The solvent is then distilled off and the residue is dissolved in a mixture of 125 ml ether and 125 ml toluene. The base is extracted with a sufficient amount of dilute sulfuric acid (20%).

The base is then separated by adding concentrated sodium hydroxide and is extracted with 125 ml ether. By adding a solution of gaseous hydrogen chloride in ether the hydrochloride is precipitated and is recrystallized from 150 to 250 ml ethanol.

The yield is 25.3 g of 7-bromo-1-methyl-2-methoxymethyl-5-(2'-chlorophenyl)-2,3-dihydro-1H-1,4-benzodiazepin in the form of its hydrochloride. Melting point 193° to 196° C.

| Bromine contents: | theoretical | 18.6% |
|---|---|---|
| | found | 18.8% |
| Chlorine contents: | theoretical | 16.4% |
| | found | 16.1% |

In a similar manner, only using sodium in ethanol instead of methanol 7-bromo-1-methyl-2-ethoxymethyl-5-(2'-chlorophenyl)-2,3-dihydro-1H-1,4-benzodiazepin can be obtained which would be identical with the product obtained in the following Example 2.

EXAMPLE 2

70 g of $N_1$-phenyl-$N_1$-methyl-$N_2$-(2'-chlorobenzoyl)-2-hydroxy-1,3-diaminopropane are heated for 2.5 hours under reflux with 350 ml phosphorus oxychloride. The excess phosphorus oxychloride is then distilled off, the residue is taken up in 400 ml chloroform and is shaken with 400 ml ice water and 200 ml concentrated sodium hydroxide. The chloroform phase is washed neutral with water, dried with sodium sulfate and concentrated. The residue (74.6 g) is dissolved in 1000 ml methylene chloride and heated upon reflux for 24 hours with 41.6 g N-bromosuccinimide. The solvent is distilled off and the residue is dissolved in a mixture of 250 ml toluene and 250 ml ether. The base is extracted with dilute hydrochloric acid (20%) and is converted into the toluene phase by treatment with concentrated sodium hydroxide and toluene. The toluene phase is then successively filtered through 150 g $Al_2O_3$ II–III (Merck Standard ) and 150 g $Al_2O_3$ I, basic (Merck Standard). After evaporating the toluene there are obtained 35.5 g of an oily mixture of 7-bromo-1-methyl-2-chloromethyl-5-(2'-chlorophenyl)-2,3-dihydro-1H-1,4-benzodiazepin and 8-bromo-1-methyl-3-chloro-6-(2'-chlorophenyl)-1,2,3,4-tetrahydro-1,5-benzodiazocin.

The mixture is then taken up in 750 ml ethanol in which previously 6.5 g of sodium have been dissolved and is heated for 24 hours upon reflux. The ethanol is then distilled off, the residue is dissolved in 300 ml chloroform and is washed neutral with water. The organic phase is then separated and dried on sodium sulfate. The solvent is distilled off and the residue (24 g) is filtered with toluene/chloroform (9:1) through 500 g aluminum oxide I (Merck Standard). After distilling off the solvent the residue is dissolved in acetone and is reacted with a solution of hydrogen chloride in ether until it has an acid reaction. The hydrochloride is thereby precipitated as a yellow crystalizate which is recovered and recrystallized from ethanol (100 to 200 ml). There is thus obtained 7-bromo-1-methyl-2-ethoxymethyl-5-(2'-chlorophenyl)-2,3-dihydro-1H-1,4-benzodiazepin as hydrochloride in a yield of 15.6 g.

| Melting point: | 191°–194° C. | |
|---|---|---|
| Bromine contents: | theoretical | 18.0% |
| | found | 18.3% |
| Chlorine contents: | theoretical | 15.9% |
| | found | 15.6% |

In a similar manner but using a solution of sodium in methanol it is possible to obtain 7-bromo-1-methyl-2-methoxymethyl-5-(2'-chlorophenyl)-2,3-dihydro-1H-1,4-benzodiazepin from the mixture consisting of 7-bromo-1-methyl-2-chloromethyl-5-(2'-chlorophenyl)-2,3-dihydro-1H-1,4-benzodiazepin and 8-bromo-1-methyl-3-chloro-6-(2'-chlorophenyl)-1,2,3,4-tetrahydro-1,5-benzodiazocin.

EXAMPLE 3

70 g of $N_1$-(4-bromophenyl)-$N_1$-methyl-$N_2$-(2'-chlorobenzoyl)-2-hydroxy-1,3-diaminopropane were refluxed for 2.5 hours in 250 ml phosphorus oxychloride. The excess phosphorus oxychloride was distilled off and the residue was stirred in 50 ml water and 500 ml methylisobutylketone until bright red crystals appeared. The crystals were collected and, as in the preceding examples stirred in chloroform, ice, water and sodium hydroxide. The residue obtained from the chloroform phase was treated with 200 ml ether and 100 g γ-alumina.

After filtration and distilling off of the solvent and oily residue (30 g) was obtained which consisted of 7-bromo-1-methyl-2-chloromethyl-5-(2'-chlorophenyl)-2,3-dihydro-1H-1,4-benzodiazepin and 8-bromo-1-methyl-3-chloro-6-(2'-chlorophenyl)-1,2,3,4-tetrahydro-1,5-benzodiazocin.

Analogous to Example 2 it was possible to obtain from the mixture, with a solution of sodium and ethanol, 7-bromo-1-methyl-2-methoxymethyl-5-(2'-chlorophenyl)-2,3-dihydro-1H-1,4-benzodiazepin or, with sodium in ethanol, 7-bromo-1-methyl-2-ethoxymethyl-5-(2'-chlorophenyl)-2,3-dihydro-1H-1,4-benzodiazepin.

EXAMPLE 4

250 g of $N_1$-methyl-$N_1$-phenyl-$N_2$-(2'-chlorobenzoyl)-2-hydroxy-1,3-diaminopropane in 500 ml of phosphorus oxychloride are refluxed for four hours. After having been poured into ice water, the solution is extracted with chloroform. The combined organic phases are washed with sodium hydroxide solution, dried over sodium sulphate and evaporated in a vacuum. 255 g of a crude product are obtained which is dissolved in 300 ml of toluene and heated under reflux for 24 hours with a solution of 50 g of sodium in 1.4 liters of methanol. The solution is then concentrated to about 3 liters and refluxed for another 7 hours with 150 g of N-bromosuccinimide. The reaction solution is washed with a dilute solution of sodium hydroxide, dried over sodium sulphate and evaporated in a vacuum until dry. The residue is taken up in toluene and filtered with γ-alumina. The toluene is distilled off, the residue taken up in 2.5 liters of acetone and the hydrochloride precipitated by passing in hydrogen chloride gas. 163.5 g of 7-bromo-1-methyl-2-methoxymethyl-5-(2'-chlorophenyl)-2,3-dihydro-1H-1,4-benzodiazepin hydrochloride are obtained.

EXAMPLE 5

151 g of $N_1$-phenyl-$N_1$-methyl-$N_2$-(2'-fluorobenzoyl)-2-hydroxy-1,3-diaminopropane are refluxed for 3 hours in 430 ml of phosphorus oxychloride, whereafter the excess phosphorus oxychloride is driven off in a vacuum. The residue is taken up in 1000 ml of chloroform and thoroughly stirred with 200 g of ice, 200 ml of water and 200 ml of a concentrated solution of sodium hydroxide. The organic phase is separated, washed until neutral with water, dried over sodium sulphate and evaporated until dry. The residue is stirred for 3 hours with 500 ml of ether, and 100 g of γ-alumina are added whereafter the mixture is filtered. After evaporation of the ether, 110 g of a crude product remain which consists of a mixture of 1-methyl-2-chloromethyl-5-(2'-fluorophenyl)-1H-2,3-dihydro-1,4-benzodiazepin and 1-methyl-3-chloro-6-(2'-fluorophenyl)-1,2,3,4-tetrahydro-1,5-benzodiazocin. The crude product is taken up in 1.5 liters of methanol in which 8.9 g of sodium had previously been dissolved and then refluxed for 5 hours. At the end of this time the solvent is distilled off, the residue dissolved in 500 ml of toluene and washed until neutral with water. The organic phase is well stirred with 200 g of alumina activity stage II–III, basic (Standard Merck) and filtered. The solvent is distilled off. The residue (93 g) which consists of 1-methyl-2-methoxymethyl-5-(2'-fluorophenyl)-1H-2,3-dihydro-1,4-benzodiazepin is dissolved in 1200 ml of methylene chloride and refluxed with 53 g of N-bromosuccinimide for 24 hours. The solvent is then distilled off and the residue dissolved in a mixture of 250 ml of ether and 250 ml of toluene from which the base is extracted with dilute hydrochloric acid (20%). By the addition of a concentrated solution of sodium hydroxide the base is separated and extracted with ether (250 ml). The hydrochloride is precipitated by adding a solution of hydrochloric acid gas in ether and finally recrystallized from 200 to 300 ml of ethanol.

The yield of 60.2 g of 7-bromo-1-methyl-2-methoxymethyl-5-(2'-fluorophenyl)-1H-2,3-dihydro-1,4-benzodiazepin in the form of its hydrochloride.

Melting point: 183°–185° C.

Elemental analysis: Calculated: C=52.3%; H=4.6%; N=6.8%; Br=19.3%; Cl=8.6% Found: C=52.3%; H=4.7%; N=6.4%; Br=19.4%; Cl=8.3%

EXAMPLE 6

70 g of $N_1$-phenyl-$N_1$-methyl-$N_2$-(2'-chlorobenzoyl)-2-hydroxy-1,3-diaminopropane and 350 ml of phosphorus oxychloride and refluxed for 2.5 hours and the excess phosphorus oxychloride is then distilled off. The residue is taken up in 400 ml of chloroform and extracted with ice water (400 ml) and 200 ml of a concentrated solution of sodium hydroxide. The chloroform phase is washed neutral with water, dried over sodium sulphate and evaporated until dry. The residue (74.6 g) is dissolved in 1000 ml of methylene chloride and refluxed for 24 hours with 41.6 g of N-bromosuccinimide. The solvent is distilled off and the residue dissolved in a mixture of 250 ml of toluene and 250 ml of ether. The base is extracted with dilute hydrochloric acid (20%) and isolated by treating the same with a concentrated solution of sodium hydroxide and toluene. The toluene phase is filtered with 150 g of Al₂O₃ II–III (Standard Merck) and 150 g of Al₂O₃ I, basic, (Standard Merck). After evaporation of the toluene, 35.5 g of an oily mixture of 7-bromo-1-methyl-2-chloromethyl-5-(2'-chlorophenyl)-1H-2,3-dihydro-1,4-benzodiazepin and 8-bromo-1-methyl-3-chloro-6-(2'-chlorophenyl)-1,2,3,4-tetrahydro-1,5-benzodiazocin are isolated and this mixture is refluxed for 24 hours with 750 ml of isopropanol in which 6.5 g of sodium have previously been dissolved. The isopropanol is then distilled off, the residue dissolved in 300 ml of chloroform and washed neutral with water. The organic phase is separated, dried over sodium sulphate and the solvent distilled off. The residue (24 g) is filtered in toluene/chloroform (9:1) with 500 g of Al₂O₃ I (Standard Merck). When the solvent has been distilled off, the residue is dissolved in acetone and treated with a solution of hydrochloric acid gas in ether until the reaction is acid. The hydrochloride simultaneously precipitates as a yellow crystalline product which is collected and recrystallized from ethanol (100–200 ml).

A yield of 15.6 g of 7-bromo-1-methyl-2-isopropoxymethyl-5-(2'-chlorophenyl)-1H-2,3-dihydro-1,4-benzodiazepin in the form of the hydrochloride is obtained. Melting point: 189°–191.5° C.

Elemental analysis: Calculated: C=52.4%; H=5.1%; N=6.1%; Br=17.4%; Cl=15.5% Found: C=52.6%; H=5.0%; N=6.0%; Br=17.2%; Cl=15.2%

The compounds of general formula I which are listed in the following Table 6 can be obtained in the same way as described in the above Examples 1 to 6.

TABLE 6

| Ex. No. | $R_3$ | $R_2$ | M.p. °C | Elemental Analysis calculated % | found % |
|---|---|---|---|---|---|
| 7 | $C_3H_7$ | Cl | 152–154 (Hydrochloride) | Cl = 15.5<br>Br = 17.4 | 15.5<br>17.1 |
| 8 | $CH_3$ | $CF_3$ | 128–130 (Hydrochloride) × ½H₂O | Cl = 7.5<br>Br = 16.9 | 7.5<br>17.2 |
| 9 | $C_2H_5$ | $CF_3$ | 102–104 | Br = 18.1 | 18.3 |
| 10 | $CH_3$ | Br | 185–187 (Hydrochloride) | Cl = 7.5<br>Br = 33.7 | 7.5<br>33.4 |
| 11 | $C_2H_5$ | Br | 154–156 (Hydrochloride) | Cl = 7.3<br>Br = 32.7 | 7.2<br>32.8 |
| 12 | $C_3H_7$ | Br | 143–146 (Hydrochloride) | Cl = 7.1<br>Br = 31.8 | 7.3<br>31.5 |
| 13 | $CH_3$ | I | 223–225 (Hydrochloride) | Cl = 6.8<br>Br = 15.3 | 6.7<br>15.7 |
| 14 | $C_2H_5$ | I | 204–207 (Hydrochloride) | Cl = 6.6<br>Br = 14.9 | 6.6<br>15.1 |

The following examples furthermore illustrate the method of the invention when applied for making compounds other than the 2-alkoxymethyl-7-bromo compounds disclosed. All of these additional compounds are characterized by a 2-hydroxymethyl substitution.

EXAMPLE 15

270 g of $N_1$-methyl-$N_1$-(4'-chlorophenyl)-$N_2$-(2'-chlorobenzoyl)-2-hydroxy-1,3-diaminopropane are introduced into 550 ml of phosphorus oxychloride with stirring and the mixture is refluxed for four hours. The solution is allowed to cool to 80° C., then poured into ice water and extracted with methylene chloride. The united organic phases are shaken with a solution of sodium hydroxide, dried over sodium sulphate and evaporated in a vacuum until dry. 275 g of a crude product are obtained and are then heated at 130° C. for 2 hours with 330 g of sodium acetate in 1.1 liter of dimethyl formamide. After filtration, the dimethyl formamide is distilled off in a vacuum, the residue dissolved in 1.2 liter of methanol and refluxed with 240 ml of a 20% sodium hydroxide solution for 30 minutes. The solution is filtered, the solvent distilled off in a vacuum, and the residue poured into 5 liters of water. The precipitated product is sucked off, washed with water and stirred for two hours with acetone, whereby 112 g of 7-chloro-1-methyl-2-hydroxymethyl-5-(2'-chlorophenyl)-2,3-dihydro-1H-1,4-benzodiazepin are obtained; the product is recrystallized from 1 liter of isopropanol and melts at 172°–174° C.

EXAMPLE 16

600 g of $N_1$-methyl-$N_1$-(4'-chlorophenyl)-$N_2$-(2'-chlorobenzoyl)-2-hydroxy-1,3-diaminopropane and 2.6 liter of phosphorus oxychloride are refluxed for 2.5 hours and the unreacted excess phosphorus oxychloride is then distilled off. The residue is taken up in chloroform and poured into ice water. The chloroform phase is separated off, dried over sodium sulphate and evaporated in vacuum until dry. The residue is then taken up in methylisobutylketone for crystallization and the crystals are removed by suction filtration. 320.7 g of a mixture of 7-chloro-1-methyl-2-chloromethyl-5-(2'-chlorophenyl)-2,3-dihydro-1H-1,4-benzodiazepin hydrochloride and 8-chloro-1-methyl-3-chloro-6-(2'-chlorophenyl)-1,2,3,4-tetrahydro-1,5-benzodiazocin hydrochloride is obtained. Another 131 g of the hydrochloride mixture can be isolated from the mother liquor.

125 g of this mixture are refluxed for 1 hour in 1.2 dioxan and 820 ml of water containing 880 ml of a 20% solution of sodium carbonate. The solvent is distilled off in a vacuum and the aqueous phase extracted with chloroform. The chloroform solution is dried over sodium sulphate and the solid residue stirred with acetone. 68.5 g of 7-chloro-1-methyl-2-hydroxymethyl-5-(2'-chloro)-phenyl)-2,3-dihydro-1H-1,4-benzodiazepin, m.p. 172°–174° C., are obtained.

EXAMPLE 17

Tablets are prepared according to the following procedure:

| Base material: | per charge |
|---|---|
| 7-Bromo-1-methyl-2-methoxymethyl-5-(2'-chlorophenyl)-1H-2,3-dihydro-1,4-benzodiazepine | 100,0 g |
| Lactose | 300,0 g |
| Maize starch | 580,0 g |
| Gelatine | 5,0 g |
| Colloidal Silicondioxide 200 | 5,0 g |
| Hydrated castor oil | 10,0 g |
| | 1000,0 g |

In the treatment of human patients dosages are ranging between 1.0 and 100 milligrams of the compound when administered perorally three times daily normally effective.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of producing compounds of the formula

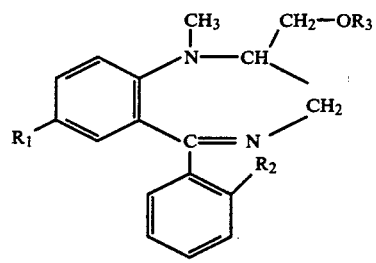

wherein R1 is hydrogen, bromine, chlorine or iodine, R2 is hydrogen, halogen or trifluoromethyl and R3 is hydrogen or primary or secondary alkyl of up to 6 carbon atoms, comprising reacting an acyldiamine of the formula

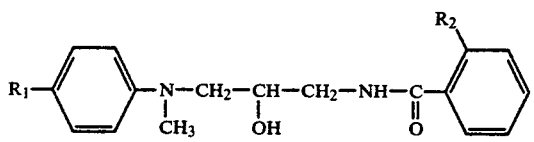

wherein R1 and R2 are as defined above, with an excess of phosphorus oxychloride sufficient to maintain the temperature throughout said reaction at the boiling point of phosphorus oxychloride, separating the mixture of isomeric compounds thus obtained of the formula

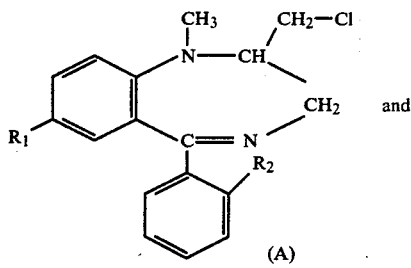

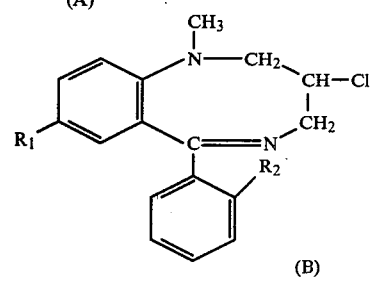

wherein R1 and R2 are as defined above; and reacting the resulting mixture in a solvent at an elevated temperature with a nucleophilic reactant selected from the groups consisting of alkali metal alkoxide, alkali metal carbonate, alkali metal hydroxide and alkali metal acetate and then reacting the reaction product of said reaction with dilute alkali metal hydroxide solution.

2. A method as claimed in claim 1, wherein the reaction of the mixture of isomeric compounds with an alkali metal alkoxide is performed in the presence of the corresponding alcohol or a solvent containing no protons.

3. A method as claimed in claim 1, wherein the mixture of isomeric compounds is reacted with an aqueous solution of an alkali metal hydroxide or alkali metal carbonate in the presence of dioxane or tetrahydrofuran.

4. A method as claimed in claim 1, wherein the mixture of isomeric compounds is reacted with sodium acetate in dimethyl formamide, and wherein the reaction mixture is then hydrolyzed with an aqueous solution of an alkali metal hydroxide in the presence of methanol.

5. A method as claimed in claim 1, wherein the mixture of isomeric compounds obtained in step 1 in which $R_2$ has the above-specified meaning and $R_1$ is hydrogen, is treated with N-bromosuccinimide or N-chlorosuccinimide or with iodomonochloride to provide a compound of formula II in which $R_1$ is bromo, chloro or iodo, respectively.

6. A method as claimed in claim 1, wherein the final compound of formula II, in which $R_1$ is hydrogen, is subsequently treated with N-bromosuccinimide, N-chlorosuccinimide or iodomonochloride to provide a compound of formula II in which $R_1$ is bromo, chloro or iodo, respectively.

7. A method as claimed in claim 1, wherein the free base is obtained by hydrolysis from the previously obtained acid addition salt of the compound of formula II.

* * * * *